(12) United States Patent
Sprenger et al.

(10) Patent No.: US 11,737,707 B2
(45) Date of Patent: Aug. 29, 2023

(54) BLOOD PRESSURE APPARATUS USING ACTIVE MATERIALS AND RELATED METHODS

(71) Applicant: Intel Corporation, Santa Clara, CA (US)

(72) Inventors: Mark E. Sprenger, Tigard, OR (US); Paul J. Gwin, Orangevale, CA (US); Aaron P. Anderson, Beaverton, OR (US); Christian Amoah-Kusi, Portland, OR (US)

(73) Assignee: INTEL CORPORATION, Santa Clara, CA (US)

( * ) Notice: Subject to any disclaimer, the term of this patent is extended or adjusted under 35 U.S.C. 154(b) by 983 days.

(21) Appl. No.: 16/576,045

(22) Filed: Sep. 19, 2019

(65) Prior Publication Data

US 2020/0146626 A1    May 14, 2020

Related U.S. Application Data

(63) Continuation of application No. 15/282,684, filed on Sep. 30, 2016, now Pat. No. 10,456,081.

(51) Int. Cl.
*A61B 5/022* (2006.01)
*A61B 5/00* (2006.01)
(Continued)

(52) U.S. Cl.
CPC .......... *A61B 5/6804* (2013.01); *A61B 5/0004* (2013.01); *A61B 5/0261* (2013.01);
(Continued)

(58) Field of Classification Search
CPC .............. A61B 5/0004; A61B 5/02208; A61B 5/02225; A61B 5/02233; A61B 5/0261;
(Continued)

(56) References Cited

U.S. PATENT DOCUMENTS 6,809,462 B2   10/2004   Pelrine et al.
10,456,081 B2  10/2019   Sprenger et al.
(Continued)

FOREIGN PATENT DOCUMENTS

CN    105706148         6/2016
DE    202012010705   *  1/2013   ......... A41D 13/1245
(Continued)

OTHER PUBLICATIONS

European Patent Office, "Communication pursuant to Article 94(3) EPC" issued in connection with European Patent Application No. 17856952.1, dated Sep. 16, 2020, 4 pages.
(Continued)

*Primary Examiner* — Eric J Messersmith
(74) *Attorney, Agent, or Firm* — Hanley, Flight & Zimmerman, LLC

(57) ABSTRACT

Example blood pressure apparatus using active materials and related methods are described herein. An example apparatus includes a band to be worn around a limb of a user, an active material carried by the band and a controller to: (1) apply an activation signal to the active material to constrict blood flow in the limb, and (2) reduce the activation signal to allow blood flow in the limb.

20 Claims, 9 Drawing Sheets

(51) Int. Cl.
*A61B 5/026* (2006.01)
*A61B 7/04* (2006.01)
*A61B 5/0265* (2006.01)

(52) U.S. Cl.
CPC ...... *A61B 5/02208* (2013.01); *A61B 5/02225* (2013.01); *A61B 5/681* (2013.01); *A61B 7/04* (2013.01); *A61B 7/045* (2013.01); *A61B 5/0265* (2013.01)

(58) Field of Classification Search
CPC ..... A61B 5/0265; A61B 5/6804; A61B 5/681; A61B 7/04; A61B 7/045
See application file for complete search history.

(56) References Cited

U.S. PATENT DOCUMENTS

| | | |
|---|---|---|
| 2009/0253996 A1 | 10/2009 | Lee et al. |
| 2010/0234714 A1 | 9/2010 | Mercier et al. |
| 2011/0021932 A1 | 1/2011 | Kim et al. |
| 2013/0053661 A1 | 2/2013 | Alberth et al. |
| 2014/0350348 A1 | 11/2014 | Tee et al. |
| 2015/0005647 A1* | 1/2015 | Gabbay ............. A61B 5/02028 600/484 |
| 2016/0033343 A1 | 2/2016 | Park et al. |
| 2016/0255944 A1* | 9/2016 | Baranski ............ A44C 5/2071 |
| 2017/0238824 A1 | 8/2017 | Woerlee et al. |

FOREIGN PATENT DOCUMENTS

| | | |
|---|---|---|
| JP | H03141925 | 6/1991 |
| JP | 2005348904 | 12/2005 |
| JP | 2006288914 | 10/2006 |
| JP | 2007125246 | 5/2007 |
| JP | 2007125246 A * | 5/2007 |
| JP | 2008237517 | 10/2008 |
| JP | 2008279061 | 11/2008 |
| WO | 2016019002 | 2/2016 |

OTHER PUBLICATIONS

International Searching Authority, "International Search Report and Written Opinion," issued in connection with International Patent Application No. PCT/2017/042116 dated Sep. 15, 2017, 12 pages.
International Searching Authority, "International Preliminary Report on Patentability", issued in connection with International Application No. PCT/US2017/042116 dated Apr. 2, 2019, 8 pages.
United States Patent and Trademark Office, "Non-Final Office Action", issued in connection with U.S. Appl. No. 15/282,684 dated Aug. 30, 2018, 10 pages.
United States Patent and Trademark Office, "Final Office Action", issued in connection with U.S. Appl. No. 15/282,684 dated Mar. 19, 2019, 10 pages.
United States Patent and Trademark Office, "Notice of Allowance and Fee(s) Due", issued in connection with U.S. Appl. No. 15/282,684 dated Jun. 19, 2019, 8 pages.
European Patent Office, "Extended European Search Report", issued in connection with application No. 17856952.1 dated Jan. 30, 2020, 8 pages.
European Patent Office, "Intention to Grant" issued in connection with European Patent Application No. 17856952.1, dated Jan. 27, 2021, 48 pages.
The State Intellectual Property Office of People's Republic of China, "The First Office Action," issued in connection with Chinese Application No. 201780053367.1, dated Jul. 5, 2021, 13 pages.

* cited by examiner

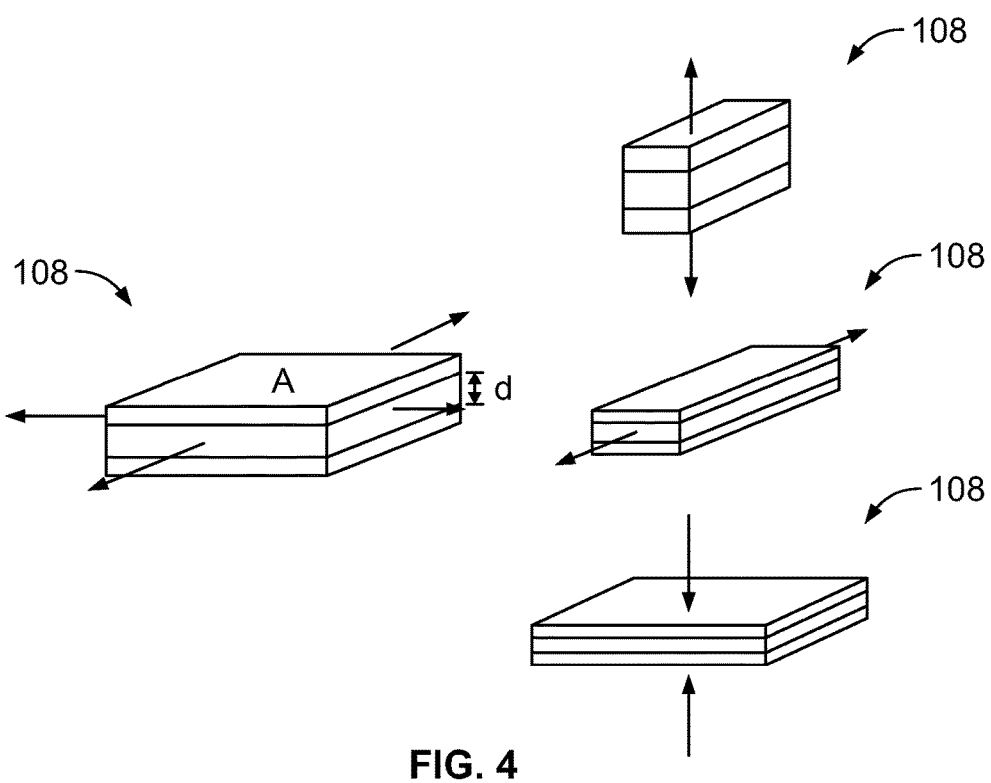
FIG. 4
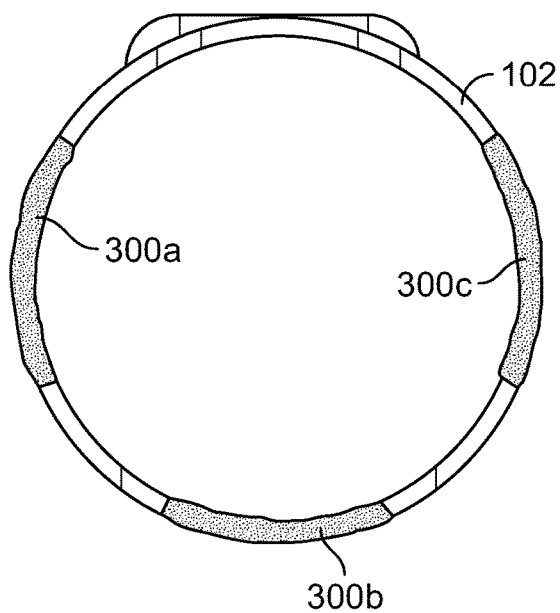
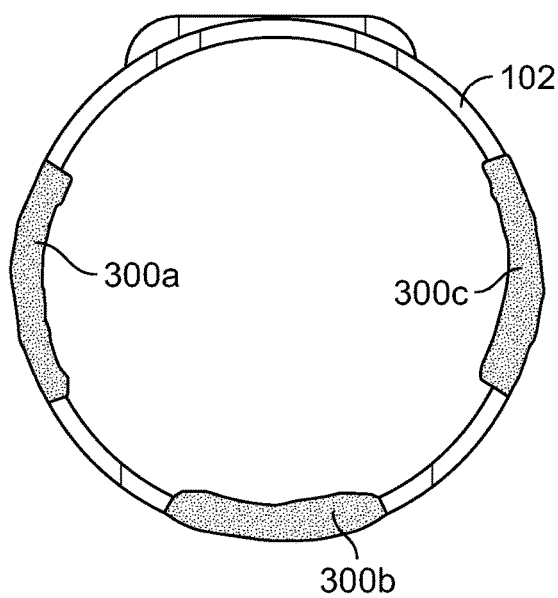
FIG. 5A  FIG. 5B

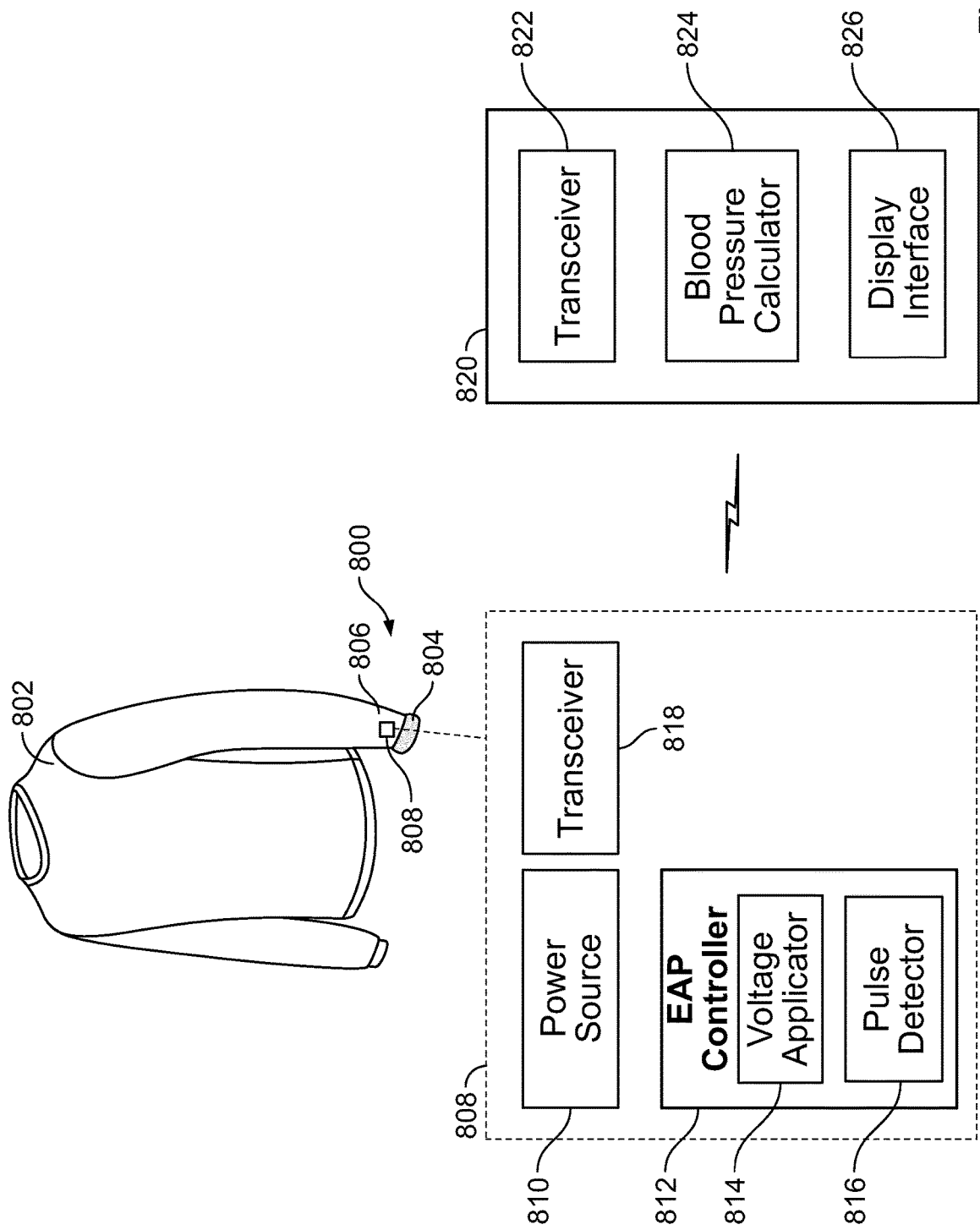

BLOOD PRESSURE APPARATUS USING ACTIVE MATERIALS AND RELATED METHODS

RELATED APPLICATION

This patent arises from a continuation of U.S. application Ser. No. 15/282,684, titled "Blood Pressure Apparatus Using Active Materials and Related Methods," filed Sep. 30, 2016, which is hereby incorporated by reference in its entirety.

FIELD OF DISCLOSURE

This disclosure relates generally to blood pressure apparatus and, more particularly, to blood pressure apparatus using active materials and related methods.

BACKGROUND

Blood pressure can be indicative of a variety of health conditions. If a person's blood pressure is too high, for instance, the pressure puts extra strain on the arteries and the heart, which may lead to heart attacks, strokes, kidney problems, etc. Low blood pressure can be related to other heart problems, endocrine problems, infections, etc. Blood pressure is commonly measured using a sphygmomanometer, which is a device that uses an inflatable cuff to collapse and then release an artery under the cuff. The cuff is wrapped around a person's arm and inflated with air. The pressure in the cuff causes a constricting force or pressure around the arm that cuts off circulation through the artery under the cuff. The pressure in the inflatable cuff is then released. While releasing the pressure, a mercury or mechanical manometer is used to measure the pressure in the cuff, which is an indirect measurement of the pressure of the blood flowing through the artery.

BRIEF DESCRIPTION OF THE DRAWINGS

FIG. 4 shows example force directions that may be applied to the example EAP of FIG. 1 to impart a capacitance change in the example EAP.

FIG. 5A is a side view of an alternative construction of the example blood pressure apparatus of FIG. 1 where multiple sections of the example band are formed by example EAP portions. In FIG. 5A, the example EAP portions are in a non-constricting state.

FIG. 5B is a side view of the example implementation of FIG. 5A in which the example EAP portions are in a constricting state.

FIG. 8 illustrates an example blood pressure apparatus incorporated into a long-sleeve shirt and constructed in accordance with the teachings of this disclosure.

Figure 1:
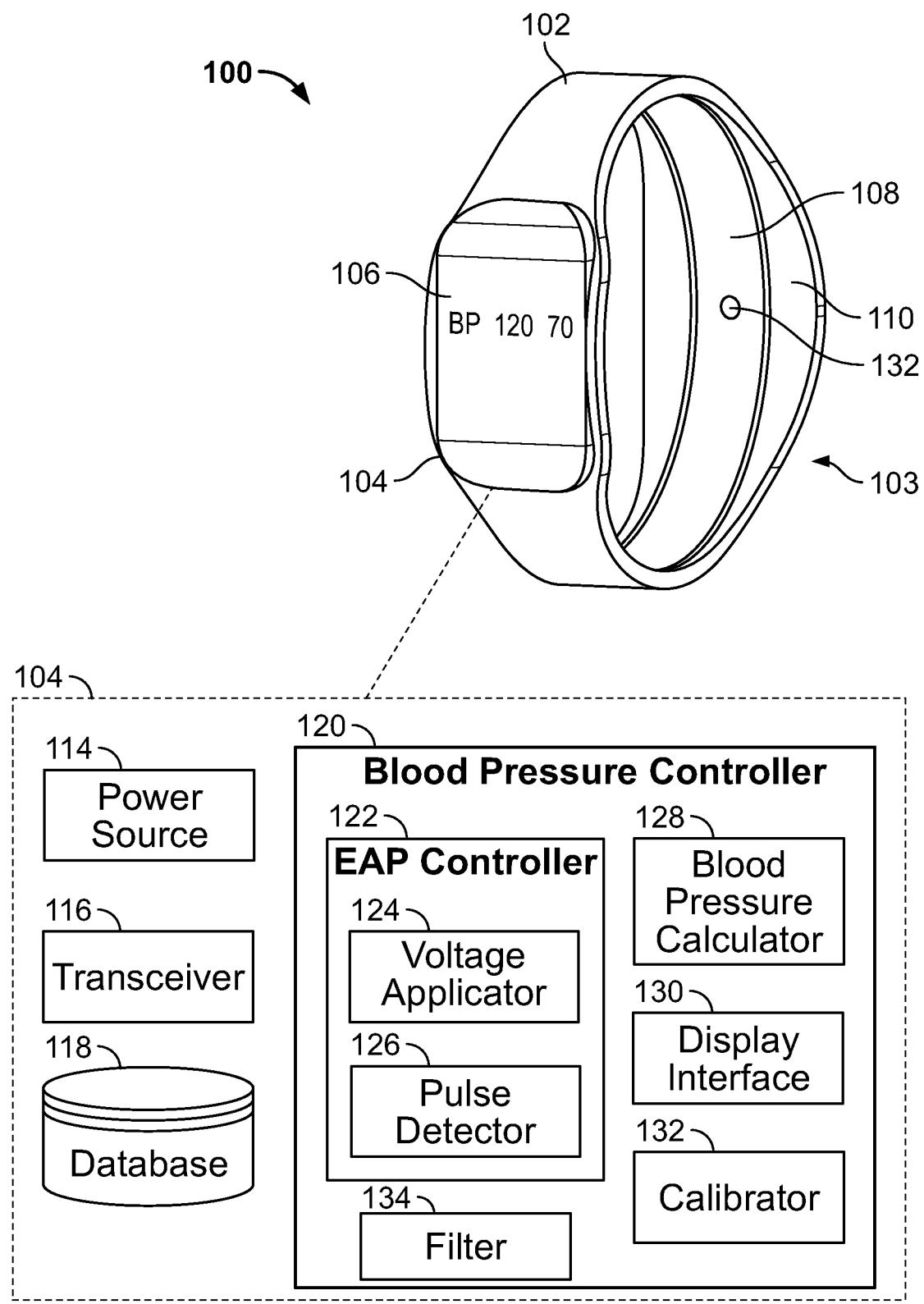
FIG. 1 illustrates an example blood pressure apparatus having an example band with an example electroactive polymer (EAP) constructed in accordance with the teachings of this disclosure.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness. Additionally, several examples have been described throughout this specification. Any features from any example may be included with, a replacement for, or otherwise combined with other features from other examples.

DETAILED DESCRIPTION

Disclosed herein are example methods, apparatus/system and articles of manufacture for determining the blood pressure of a user. Example blood pressure apparatus disclosed herein include relatively small, compact devices that can be worn by a user and used, when desired, to determine the user's blood pressure. Example blood pressure apparatus may be worn, for example, around a user's wrist, upper arm, etc. and/or incorporated into an article of clothing. The example blood pressure apparatus employ active materials that deform, when activated, to apply a constricting force to cutoff blood flow in the user's limb. The pressure provided by the active material is released, and the example blood pressure apparatus may be used to sense the blood flow through the user's artery and, thus, determine the user's blood pressure. Before describing the various details of the present disclosure, a brief overview of blood pressure calculation is provided.

In general, a blood pressure measurement (also referred to as a reading or value) contains two numbers, usually written as a ratio, which include the systolic pressure and the diastolic pressure. The systolic pressure, which is the top number, represents the pressure in the arteries when the heart beats (i.e., when the heart muscle contracts). The diastolic pressure, which is the bottom number, represents the pressure in the arteries between heart beats (i.e., when the heart muscle is resting between beats and refilling with blood). The pressures are typically measured in millimeters of mercury (mm Hg). A common blood pressure measurement is 120/80 mm Hg, for example.

Two known techniques are commonly employed for determining blood pressure: the oscillatory technique and the Korotkoff technique. In both techniques, a limb (e.g., an arm) of a user is constricted to block blood flow through the arteries in the limb. For instance, using a sphygmomanometer, an inflatable cuff is placed around an upper arm of a user and pressurized to restrict blood flow through the arteries in the arm. The pressure in the inflatable cuff is then slowly released. As the pressure is reduced, blood begins to flow through the arteries in the arm again. The Korotkoff technique involves listening to the sound of the blood flow to determine the systolic and diastolic pressures. In particular, there are five Korotkoff sounds (however, only the first and last sounds are of clinical significance). The systolic blood pressure is taken to be the first Korotkoff sound that is first heard and the diastolic blood pressure is the pressure at which the fourth Korotkoff sound is barely audible. The oscillatory technique, on the other hand, involves measuring the pressure oscillations of the pumping blood, which may be detected with a sensor.

In recent years, wearable devices in the health and fitness market have become popular. These known devices include sensors for detecting heart rate, SP02% and other measures of performance and health metrics. However, these known wearable devices have not been able to incorporate blood pressure measurements. To produce enough constricting force, known blood pressure devices use a cuff that is wrapped around the arm of a user and inflated. These known blood pressure devices are relatively large and uncomfortable and, thus, are only used when taking the blood pressure of a person, such as at a hospital (or other medical facility) or at the person's home when convenient. Additionally, the pneumatic cuff requires significant power to operate and is generally complicated to use. Therefore, blood pressure devices have not been incorporated into wearable devices.

Example blood pressure apparatus disclosed herein include a band to be worn around a limb (e.g., an arm (the wrist, upper arm, etc.), a leg, etc.) of a user and an active material. To create a constricting force, the example blood pressure apparatus employ an active material that is coupled to the band. As used herein, the term "active material" refers to a material that exhibits a reversible change in a fundamental property such as dimension, shape, orientation, shear force, or flexural modulus upon application or removal of an activation signal. An active material may include, for example, a shape-memory alloy (SMA) (also referred to as a smart memory alloy) or an electroactive polymer (EAP). When activated, the active material deforms or morphs shape to provide pressure around the limb of the user. The activation may then be decreased to release the constricting force around the limb and allow blood flow through the artery. The blood pressure apparatus detects the blood flow and determines the user's blood pressure. The example blood pressure apparatus may determine the user's blood pressure using either the oscillatory technique or the Korotkoff technique. In some examples, the active material is used to sense pulses or oscillations caused by the blood flow when reducing the activation of the active material. In other examples, one or more sensors (e.g., a microphone) are coupled to the band to detect the blood flow in the limb of the user.

Depending on the particular type of active material, an activation signal is used to activate the activate material, thereby causing the active material to change shape (e.g., deform). The activation signal may be, for example, application of an electric current or voltage, a temperature change, a magnetic field, a mechanical loading or stressing, etc. For example, when using an SMA, a heat signal or a voltage may be applied for changing the property of the SMA. When using an EAP, for example, a voltage may be applied for changing the property of the EAP.

In some examples, the change in the property of the active material remains for the duration of the applied activation signal. In some examples, when the activation signal is ceased (e.g., when the active material is deactivated), the property of the active material reverts to an unpowered form and returns substantially to its original property. In some examples, a return mechanism (e.g., a spring) capable of providing a force opposite to the actuation force of the active material is provided.

Some example apparatus disclosed herein incorporate an active material band into a garment, such as a shirt. For example, the active material band may be coupled to a sleeve of the shirt and positioned to be worn around an upper arm of the user. The active material band may be activated, via an activation signal, to provide a constricting force around the arm of the user. The activation signal may then be reduced to allow blood flow through the arm, which is detected and used to determine the blood pressure of the user.

Unlike known pneumatic blood pressure devices, example blood pressure apparatus disclosed herein do not require manual activation (e.g., pumping of air) or complicated pneumatic machines to produce constricting pressure. Instead, the example blood pressure apparatus employ active materials that are relatively small, lightweight and produce strong constricting force. As a result, the example blood pressure apparatus are more comfortable to wear and may be worn by a user for a longer period of time (e.g., throughout the day) compared to known blood pressure devices. Further, the example blood pressure apparatus are more energy efficient than known blood pressure devices.

Turning now to the figures, FIG. 1 illustrates an example blood pressure (BP) apparatus 100 constructed in accordance with the teachings of this disclosure. The example BP apparatus 100 includes a band 102 to be worn around a body part or limb (e.g., an arm, a leg, etc.) of a user. The band 102 forms an opening 103 through which the user's limb can be inserted. In the illustrated example, the BP apparatus 100 includes an electronics unit 104 and a display 106 coupled to the band 102, disclosed in further detail herein.

Figure 2A:
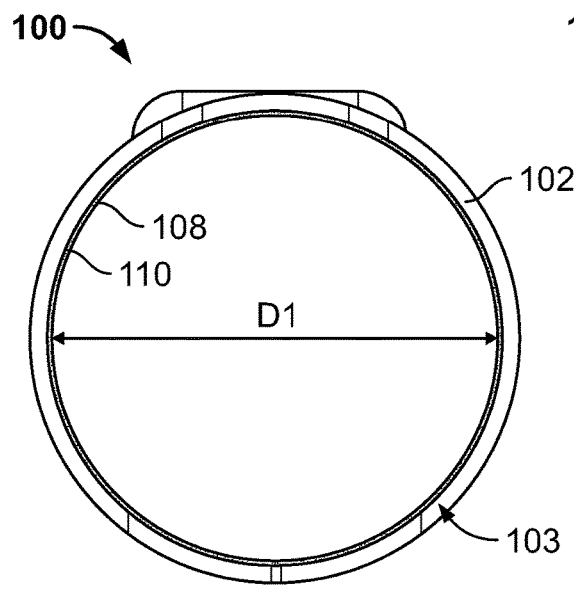
FIG. 2A is a side view of the example blood pressure apparatus of FIG. 1 in which the example EAP is in a non-constricting state.
Figure 2B:
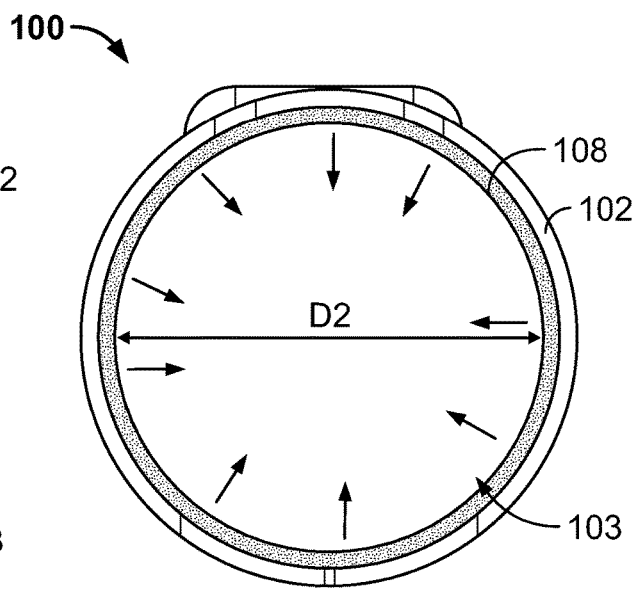
FIG. 2B is a side view of the example blood pressure apparatus of FIG. 1 in which the example EAP is in a constricting state.

To constrict blood flow in the limb of the user, the example BP apparatus 100 includes an active material carried by the band 102. In the BP apparatus 100 of FIG. 1, the active material is implemented using an electroactive polymer (EAP) material. In particular, in the illustrated example, an EAP 108 (e.g., an EAP strip or band) is disposed on an inner surface 110 of the band 102 and, thus, around the opening 103. When an activation signal is applied to the EAP 108, the EAP 108 changes shape (e.g., bends, deforms, etc.). In particular, the EAP 108 changes between a non-constricting state or shape (e.g., a relaxed state, a deactivated state, etc.) and a constricting state or shape (e.g., an activated state, restricted, etc.). FIG. 2A shows the EAP 108 of the BP apparatus 100 in the non-constricting state and FIG. 2B shows the EAP 108 of the BP apparatus 100 in the constricting state. In in the non-constricting state illustrated in FIG. 2, the EAP 108 is substantially flush or even with the inner surface 110 of the band 102. When the EAP 108 is activated, the EAP 108 deforms or compresses inward, thereby decreasing a diameter of the opening 103 from a first diameter D1, as illustrated in FIG. 2A, to second, smaller diameter D2, as illustrated in FIG. 2B. In the illustrated example, the band 102 is relatively rigid, so that change in shape of the EAP 108 is focused inward to decrease the diameter or circumference of the opening 103. The EAP 108 deforms more or less depending on the strength of the activation signal. The EAP 108 can be deformed an amount sufficient to restrict or cutoff blood flow in the limb of the user. In particular, the EAP 108 may be activated to a degree in which blood flow in an artery under the band 102 is stopped. Once blood flow is cutoff, the strength of the activation signal can be decreased to reduce the pressure applied by the EAP 108 and to allow blood flow through the artery again. While reducing the pressure, one or more blood pressure measurements may be taken, as disclosed in further detail herein.

The EAP 108 may be constructed of, for example, an insulating polymer and/or rubber that deforms in response to an activation signal (e.g., an electrostatic force). The EAP 108 may include, for example, silicone elastomers, acrylic elastomers, polyurethanes, thermoplastic elastomers, copolymers including polyvinylidene fluoride (PVDF), pressure-sensitive adhesives, fluoroelastomers, and/or polymers comprising silicone and acrylic moieties (e.g., copolymers including silicone and acrylic moieties, polymer blends including a silicone elastomer and an acrylic elastomer).

In some instances, a pressure of about 180-220 mm HG (or 3.5-4.25 pounds per square inch (psi)) is needed to provide proper construction around the limb of the user. The force equation of an EAP is St=pr, where S is the strength or force capacity of the EAP material, t is the thickness of the EAP material, p is the force generated by the EAP material, and r is the radius of the EAP. In some examples, the force capacity S of the EAP may range from about 0.1-3 mega pascal (Mpa) (or 14.5-435 psi). A typical wrist radius r is about 1 inch. Therefore, as an example, using a force generated p of 4.25 psi (the force needed to constrict blood flow), a radius r of 1 inch, and an EAP having a force capacity S of 200 psi, the thickness t is about 0.02 inches (or 0.54 millimeters (mm)). Thus, if the EAP 108 has a force capacity of 200 psi, a thickness of 0.02 inches and a radius of 1 inch, the EAP 108 generates a force of about 4.25 psi, which is sufficient force to constrict blood flow in the limb of the user. In other examples, the force capacity S, the thickness t, the forced generated p, and the radius r may be different, depending on the desired parameters. For example, the thickness t of the EAP 108 and/or the force capacity S may be increased to increase the force generated p. In some examples, the EAP 108 generates twice the pressure required to constrict the limb of the user. Additionally, in some examples, the width of the band 102 can be sized to provide the required force density.

Referring back to FIG. 1, the electronics unit 104 of the example BP apparatus 100 includes a power source 114 (e.g., a battery), a transceiver 116, a database 118 and a blood pressure controller 120 to determine a blood pressure of the user. In the illustrated example, the blood pressure controller 120 includes an EAP controller 122, which includes a voltage applicator 124 and a pulse detector 126 (e.g., a pulse sensor), a blood pressure calculator 128, a display interface 130, a calibrator 132 and a filter 134. The EAP controller 122 controls the EAP 108 to activate (e.g., deform) the EAP 108 or deactivate the EAP 108. In particular, the voltage applicator 124 applies an activation signal, in the form of a voltage or current, to the EAP 108 to activate the EAP 108 and change the shape of the EAP 108. The more voltage applied to the EAP 108, the more the EAP 108 is distorted, thereby causing more restriction on the limb of the user. Once activated to a desired shape that constricts blood flow, the voltage applicator 124 decreases the voltage (e.g., at a relatively slow rate) to allow blood flow through the limb of the user. While the voltage applicator 124 decreases the voltage (e.g., reducing the activation signal), the pulse detector 126 detects or measures pressure pulses or oscillations generated by the flow of blood through the artery. In particular, the EAP 108 acts as a sensor and may be used to detect pressure changes of the limb acting back on the EAP 108. When force or pressure is applied to the EAP 108, the force generates a capacitance change in the EAP 108, which is detected by the pulse detector 126, as disclosed in further detail herein.

The blood pressure calculator 128 determines the blood pressure value (e.g., the ratio of systolic to diastolic pressure) based on the voltage applied by the voltage applicator 124, which corresponds to a pressure applied to the limb, and the pulse(s) detected by the pulse detector 126. In other words, the voltage applied to the EAP 108 equates to a specific pressure applied on the limb, and when pulses in the blood are sensed by the pulse detector 126, the pressure applied by the EAP 108 can be correlated to a corresponding blood pressure. Thus, the systolic pressure and the diastolic pressure (and/or any other phases of pressure) can be identified. In some examples, the blood pressure measurement is stored in the database 118.

The display interface 130 controls the information displayed on the display 106. The display interface 130 causes the display 106 to present the blood pressure determined by the blood pressure calculator 128. In some examples, the display 106 receives input from a user. For example, a user may select to determine his/her blood pressure. Once requested, the EAP controller 122 and the blood pressure calculator 128 determine the blood pressure as described herein. Additionally or alternatively, the determined blood pressure (and/or any of the other data) may be transmitted via the transceiver 116 to another electronic device, such as a smart phone, a computer, etc. The transceiver 116 may be, for example, a Bluetooth® transceiver. In some examples, the transceiver 116 receives a blood pressure request from the other electronic device. For example, a user may request a blood pressure reading via his/her phone, which transmits the request to the BP apparatus 100.

In some examples, the display 106 presents other information and/or includes other features (sometimes referred to as complications). The display 106 can display other health or fitness related information, for example. In some examples, the BP apparatus 100 is considered a wrist watch and can be worn on the wrist of the user. The display 106 may be a display of a digital watch or smart watch. In other examples, the band 102 can be wider or smaller and be worn on another part of the arm, the leg, the neck and/or another body part. In the illustrated example, the band 102 forms a continuous loop. In other examples, the band 102 includes a break and includes a fastener or lock to couple two sections of the band 102, similar to a watch band.

Figure 3:
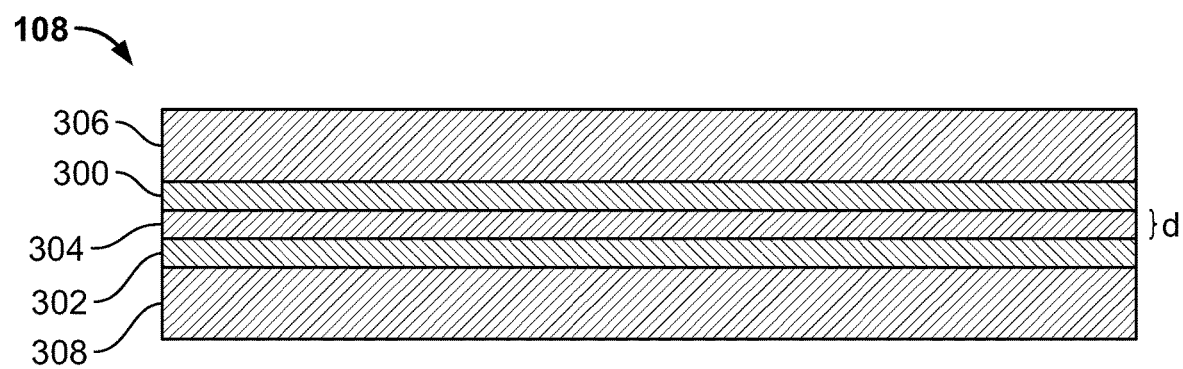
FIG. 3 is a cross-sectional view of a section of the example EAP of FIG. 1.

A cross-section of a portion of the example EAP 108 is illustrated in FIG. 3. In general, the EAP 108 is a flexible capacitor that is a composite construction of a thin elastomer such as silicone, an electrode such as exfoliated graphite compounded with silicone, and a dielectric insulator such as silicone, Mylar, etc. In the illustrated example, the EAP 108 includes a first charge plate 300 (e.g., an electrode), a second charge plate 302, a dielectric 304 between the first and second charge plates 300, 302, a first insulation layer 306 on one side and a second insulation layer 308 on the opposite side. The arrangement of the materials creates a capacitor with an inner dielectric, a charge plate on each side of the dielectric, and an insulator on the outer sides of the charge plates. The first and/or second charge plates 300, 302 may be constructed of, for example, graphite silicone, an exfoliated graphite compounded with silicone, silicone and a conducting medium (e.g., carbon) and/or any other suitable electrode material. The dielectric 304 may be constructed of, for example, silicone, an amorphous polymer and/or other suitable dielectric. The insulator may be constructed of, for example, silicone, polydimethylsiloxane (PDMS) and/or any other suitable insulator material.

In some examples, the thickness of the EAP 108 is about 500 micrometers (μm). In other examples, the thickness of the EAP may be smaller or larger. In some examples, depending on the layering, the EAP 108 is highly flexible. In some examples, the first and second insulation layers 306, 308 correspond to the material of the band 102 (FIG. 1). In other words, the first and second charge plates 300, 302 and the dielectric 304 may be embedded (e.g., molded into) the material (e.g., silicone) of the band 102. In other examples, the EAP 108, including the first and second insulation layers 306, 308, may be coupled the inner surface 110 of the band 102 or embedded in the material of the band 102.

When a voltage (e.g., an activation signal) is applied to the first and second charge plates 300, 302, the first and second charge plates 300, 302 move relative to each other, thereby creating a force that morphs the shape of the EAP 108. In particular, when a voltage is applied to the EAP 108, the first and second charge plates 300, 302 move toward each other, which morphs the EAP 108 and causes the EAP 108 to flex radially inward to the constricting state (FIG. 2B). When a strength of the voltage is reduced, the first and second charge plates 300, 302 move away from each other, such that the shape of the EAP 108 morphs back to the non-constricting state (FIG. 2A). Additionally, the EAP 108 acts as a sensor to sense or detect forces applied to the EAP 108. In particular, when an external force is applied to the EAP 108 that changes the shape of the EAP 108, a change in voltage or capacitance is generated. The capacitance in the EAP 108 is a function of the area of the charge plates 300, 302 (e.g., the electrode area), the voltage in the charge plates 300, 302 (e.g., the electrode charge), a distance d (FIG. 3) between the charge plates 300, 302, and the permittivity of the volume between the charge plates 300, 302. When a force is exerted on the EAP 108, the area of the first charge plate 300 and/or the second charge plate 302 deforms and the distance d changes, thereby changing the capacitance of the EAP 108. This change in capacitance is sensed or detected by the pulse detector 126. Therefore, the reactive force (e.g., a pulse) of the blood flow acting on the EAP 108 produces a capacitance change, which can be sensed by the pulse detector 126. In some examples, the first insulation layer 306 is the inner layer that faces the opening 103 (FIG. 1) where the limb of the user is disposed, and the second insulation layer 308 is the outer layer that faces the inner surface 110 of the band 102 (FIG. 1). In some examples, the second insulation layer 308 is relatively rigid, which moderates the shape factor imparting a load on the EAP 108.

Further, the direction of the force applied to the EAP 108 and the resulting shape change affects the resultant capacitance. In other words, a force of the same magnitude applied in different directions may produce different capacitance changes. FIG. 4 illustrates example force vectors that cause a change in capacitance in the EAP 108. Although the force magnitudes may be the same, the resultant capacitance may be different. As such, the EAP 108 may not only be used to detect a force applied to the EAP 108, but also a direction of the force applied to the EAP 108. In some examples, prior to using the BP apparatus 100, the EAP 108 may be tested or calibrated by applying various amounts of force in various direction to the EAP 108. Each combination of force and direction generates a unique force signature, which may be stored in the database 118 (FIG. 1), for example. A sensed change in capacitance can be compared to the force signatures to determine the amount of force and/or direction being applied to the EAP 108.

In some examples, the EAP 108 is constructed of a plurality of individual EAP cells (e.g., a matrix of EAP cells). Therefore, different forces can be detected by different ones of the EAP cells. As a result, the pulse detector 126 can detect a variation in capacitance of neighboring regions and determine the magnitude, the direction and/or the location of the force. In some examples, the EAP cells are orientated in the same direction and arranged along a common plane. In other examples, one or more of the EAP cells may be orientated differently (e.g. perpendicular to a neighboring EAP cell), which may enhance the ability to detect the direction in which the force is applied. As mentioned above, the type of loading (direction and/or shape deformation characteristics) can be calibrated, patterned, and sensed for intelligent interpretation of the force signatures, yielding greater usability.

In some examples, the BP apparatus 100 calibrates itself based on resistance drift, which is a change in the resistivity of the first and second charge plates 300, 302 (e.g., electrode resistivity). Resistance drift occurs as a function of cycle count (e.g., in the millions) of fatigue cycles, water ($H_2O$) content, and temperature change. The calibrator 132 measures the resistance of the EAP 108 and uses any change in resistance to adjust the capacitance measurements. In other words, the EAP 108 can be calibrated as changes in the plate resistivity occur. In some examples, the resistivity is sensed simultaneously with the dynamic capacitance change while the EAP 108 is physically distorted. Because the resistivity changes corresponding to the type of deformation, the resistivity can be used to determine if the capacitance changed due to compressive or tensile deformation of the sensor.

In some examples, in addition to or as an alternative to detecting blood flow pulses with the EAP 108, one or more sensors are provided to detect blood flow in the limb of the user. For example, in the illustrated example of FIG. 1, a microphone 132 is disposed on the inner surface 110 of the band 102. When the band 102 is worn on the limb of the user, the microphone 132 is in contact (or relatively close) to the skin of the user and can detect the Korotkoff sounds. The blood pressure calculator 128 may determine the blood pressure based on the voltage applied by the voltage applicator 124 and the timing of the sounds detected by the microphone 132. In other examples, other types of sensors may be employed. For example, an infrared (IR) sensor may be used to detect blood flow based on temperature changes. In other examples, the sensor may be disposed in other locations. Thus, the example BP apparatus 100 may be used to determine blood pressure using the Korotkoff technique and/or the oscillatory technique.

In some examples, the filter 134 (FIG. 1) filters signals from the capacitance change that are not associated with the desired pulses. For instance, if a user moves his/her arm or flexes his/her arm, the force from the user's arm may generate a capacitance change in the EAP 108 that could inadvertently distort the blood pressure calculation. The filter 134 recognizes the signal profile of such a movement and removes the undesired signal(s). For example, a signal generated by a flexing of the arm may have a particular shape (e.g., a large rise over a long period of time) and/or may occur at a different frequency (e.g., 1 per second) than signals generated by the pulse (e.g., 10 per second). In some examples, the filter 134 decomposes the overall signal into the individual signals, maps and compares the signatures of those signals to an expected pulse signature (e.g., a range or threshold) and removes any signal(s) (e.g., extraneous data) outside of the bounds or limits of the expected pulse signature. In some examples, if an arm flexing or movement is detected in the signal (which may result in an increased pressure on the arm because of the arm enlarging), the EAP controller 122 reduces the activation signal to the EAP 108 to result in the desired pressure on the arm.

In the illustrated example of FIGS. 1, 2A and 2B, the EAP 108 is disposed in a continuous loop around the inner surface 110 of the band 102. In other examples, the EAP 108 may be separated into one or more smaller portions distributed around the inner surface 110 of the band 102. Additionally or alternatively, the EAP 108 may form one or more segments of the band 102. For example, FIGS. 5A and 5B illustrate an example construction in which three EAP portions 500a, 500b, 500c form individual parts (e.g., chain links, segments, etc.) of the band 102. FIG. 5A shows the EAP portions 500a, 500b, 500c in a non-constricting state, and FIG. 5B shows the EAP portions 500a, 500b, 500c in the constricting state. Similar to the operation of the EAP 108 in FIGS. 2A and 2B, when the EAP portions 500a, 500b, 500c are activated, the EAP portions 500a, 500b, 500c deform and decrease an inner diameter of the band 102, thereby restricting blood flow through the limb of the user.

Figure 6:
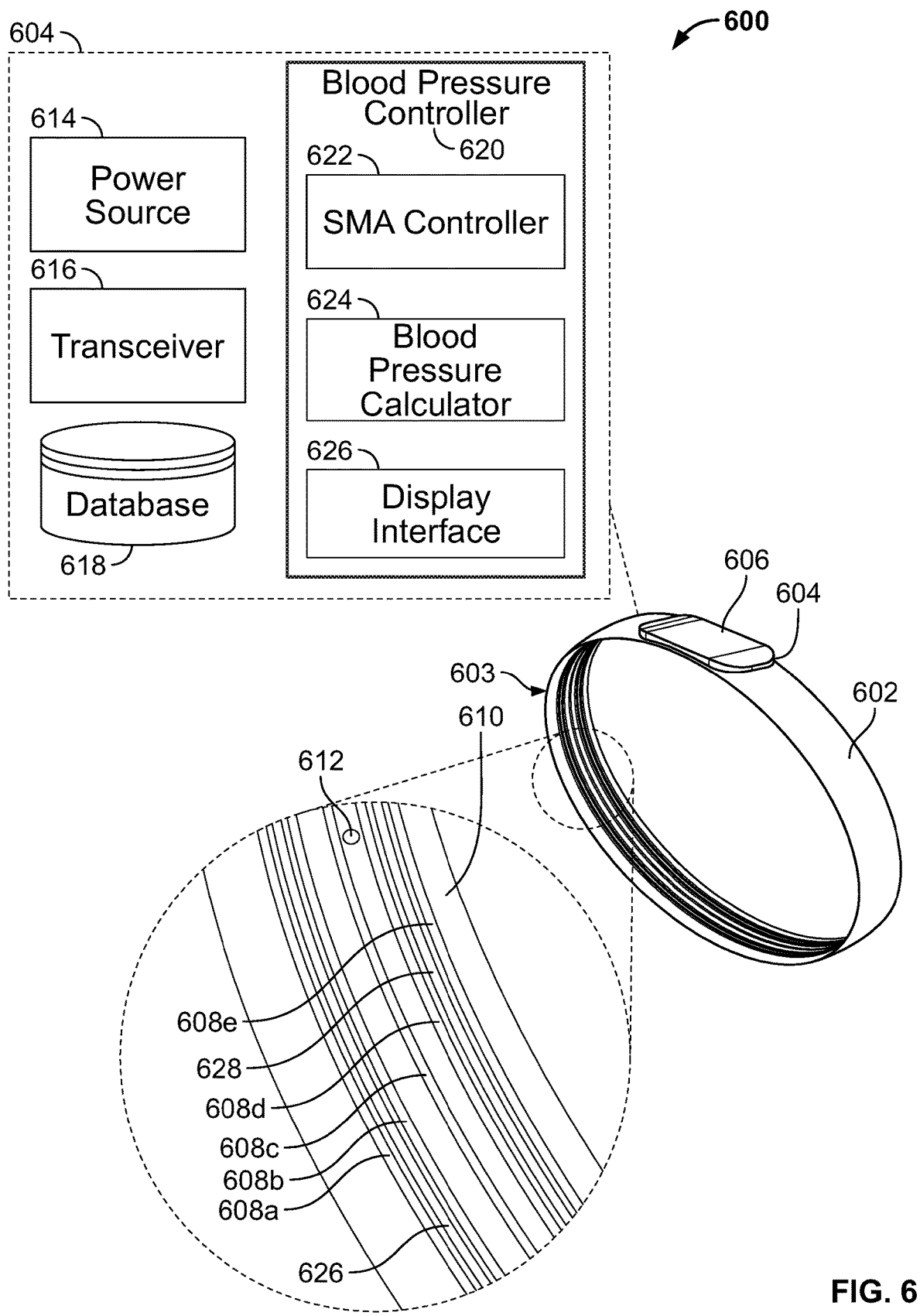
FIG. 6 illustrates an example blood pressure apparatus having an example band with example shape-memory alloy (SMA) wires constructed in accordance with the teachings of this disclosure.
Figure 7A:
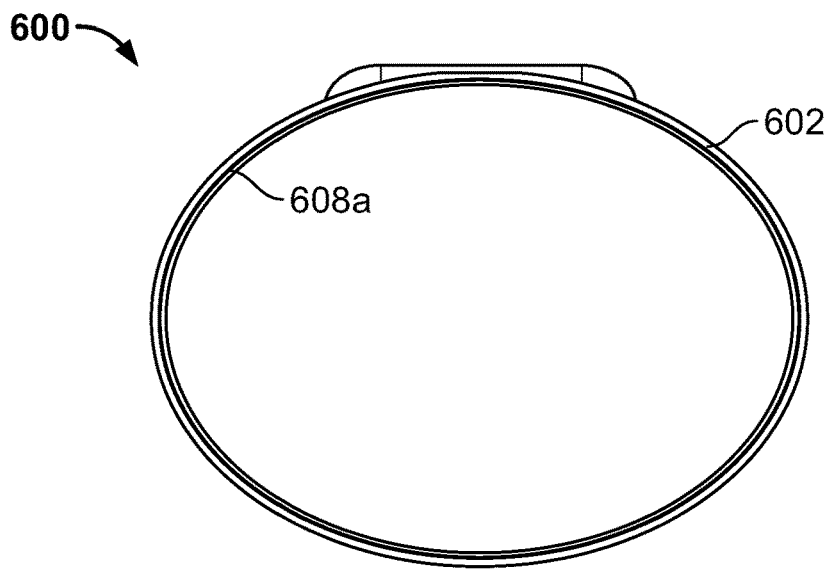
FIG. 7A is a side view of the example blood pressure apparatus of FIG. 6 showing the example band when the example SMA wires are in a non-constricting state.
Figure 7B:
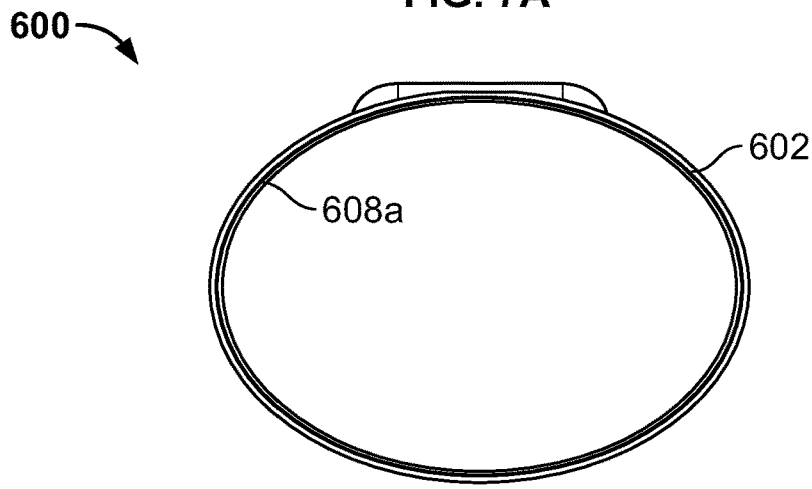
FIG. 7B is a side view of the example blood pressure apparatus of FIG. 6 showing the band when the example SMA wires are in a constricting state.
Figure 7C:
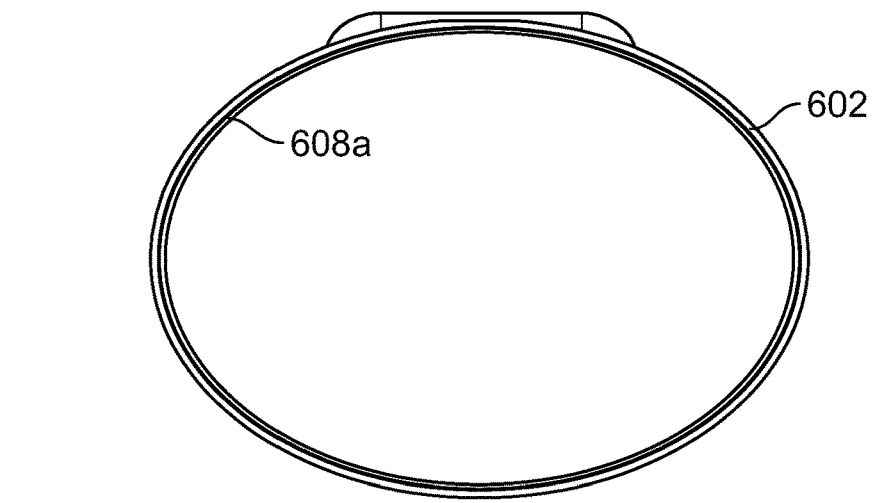
FIG. 7C is a side view of the example blood pressure apparatus of FIG. 6 showing the example band after the SMA wires have been released back to the non-constricting state.

FIG. 6 illustrates another example BP apparatus 600 constructed in accordance with the teachings of this disclosure. Similar to the BP apparatus 100 (FIG. 1), the BP apparatus 600 includes a band 602 (forming an opening 603) to be worn on a body part or limb of a user, an electronics unit 604 and a display 606 coupled to the band 602, and an active material to provide constricting force to the limb of the user. In the BP apparatus 600 of FIG. 6, the active material is implemented using an SMA. In particular, in the illustrated example, an SMA wire 608a (e.g., an SMA ring) is coupled to the band 602. In the illustrated example, the SMA wire 608a forms a complete or continuous loop around an inner surface 610 of the band 602. When an activation signal is applied to the SMA wire 608a, the SMA wire 608a changes shape. In particular, the SMA wire 608a changes between a non-constricting state and a constricting state. FIG. 7A shows the band 602 of the BP apparatus 600 when the SMA wire 608a is in the non-constricting state, and FIG. 7B shows the band 102 of the BP apparatus 600 when the SMA wire 608a is in the constricting state. In the illustrated example, the band 602 is relatively flexible. As illustrated in the constricting state of FIG. 7B, the shape of the SMA wire 608a is changed such that the diameter or circumference of the band 602 and the SMA wire 608a is reduced, which enables the band 602 and the SMA wire 608a to restrict blood flow in the limb of the user. When the activation signal is reduced, the SMA wire 608a returns to the non-constricting state, as illustrated in FIG. 7C.

In the illustrated example of FIG. 6, multiple SMA wires are employed. In particular, five SMA wires are employed: a first SMA wire 608a, a second SMA wire 608b, a third SMA wire 608c, a fourth SMA wire 608d, and a fifth SMA wire 608e. The second, third, fourth and fifth SMA wires 608b-608e operate substantially the same as the first SMA wire 608 described above. In other examples, more or fewer SMA wires may be implemented. The SMAs wires 608a-608e include an inner SMA material and an outer layer of insulation. The SMA material may include a nickel-titanium based alloy, an indium-titanium based alloy, a nickel-aluminum based alloy, a nickel-gallium based alloy, a copper based alloy (e.g., a copper-zinc alloy, a copper-aluminum alloy, copper-gold, and copper-tin alloys), a gold-cadmium based alloy, a silver-cadmium based alloy, an indium-cadmium based alloy, a manganese-copper based alloy, an iron-platinum based alloy and/or an iron-palladium based alloy. In some examples, employing multiple smaller SMA wires, as opposed to one larger SMA wire, reduces the energy consumption, thus making the BP apparatus 600 more energy efficient.

Below is an example calculation to determine a diameter of an SMA wire to that produces a force of 4.25 psi for constricting the blood flow of a user. Assume, for example, a wrist diameter, WristDiameter, of 190 mm and a band diameter (e.g., the diameter of the band 602), $Band_D$, of 40 mm, then an area of an SMA wire, $Band_A$ (in square meters (m²)), can be calculated using Equation 1:

$$Band_A = WristDiameter \cdot Band_D = 0.008 m^2 \qquad \text{Equation 1}$$

With $Band_A$ known, the force on the wrist, WristForce (in Newtons (N)), can be calculated using Equation 2:

$$WristForce = 4.25 psi \cdot Band_A = 222.701 N \qquad \text{Equation 2}$$

The WristForce can be divided by gravity (9.80665 m/s²) to give a mass of 22.709 kilograms (kg). Assuming, the SMA wire has a strain, $SMA_{strain}$, of 0.01 (mm/mm or in/in), then the stress generated by the SMA wire, $SMA_{StressGeneration}$, can be calculated using Equation 3:

$$SMA_{StressGeneration} = \frac{\text{Pull Force}}{\text{Total}_{WireArea}} = \frac{7 \, mg \cdot g}{\pi \left(\frac{0.001 \, in}{2}\right)^2} = 1.355 \cdot 10^8 \, Pa \qquad \text{Equation 3}$$

$Total_{WireArea}$ is the total area of the SMA wire, and PullForce is the maximum pulling force for a given wire diameter. For example, with a wire diameter of 0.001 in, a force of 7 mg (gram-force) can be generated. The 7 mg is multiplied by gravity (g) for unit conversion. Solving for the $Total_{WireArea}$ gives Equation 4:

$$Total_{WireArea} = \frac{WristForce}{SMA_{StressGeneration}} = 1.644 \cdot 10^{-6} m^2 \qquad \text{Equation 4}$$

The $Total_{WireArea}$ from Equation 3 can be inserted into Equation 4 to solve for the WireDiameter as shown in Equation 5:

$$WireDiameter = 2 \cdot \sqrt{\frac{\frac{WristForce}{SMA_{StressGeneration}}}{\pi}} = 0.057 \, in \qquad \text{Equation 5}$$

Therefore, a WireDiameter of 0.057 in produces a force of 4.25 psi. The WireDiameter can correspond to a single SMA wire, or can be scaled (based on area) into a plurality of SMA wires. Therefore, a plurality of smaller SMA wires (e.g., the SMA wires 608a-608e) with an equivalent diameter of 0.057 in can be utilized to generate the same force.

To detect the blood flow in the limb while the SMA wires 608a-608e transition between the constricting state and the non-constricting state, the BP apparatus 600 includes a sensor. In the illustrated example, the sensor is implemented as a microphone 612. The microphone 612 detects the Korotkoff sounds indicative of blood flow. In other examples, other types of sensors may be implemented, such an infrared (IR) sensor that detects the temperature of the blood, an EAP (e.g., similar to the EAP 108 disclosed above), etc. For instance, an EAP may be coupled to the band 602 to detect forces (e.g., via a change in capacitance) imparted by the limb of the user on the band 602. In the illustrated example, the microphone 612 is disposed on the inner surface 610 of the band 102 near a side or bottom of the band 602. In other examples, the microphone 612 may be disposed in other locations along the band 602.

In the illustrated example of FIG. 6, the electronics unit 604 includes a power source 614 (e.g., a battery), a transceiver 616, a database 618 and a blood pressure controller 620 to determine a blood pressure of the user. In the illustrated example, the blood pressure controller 620 includes an SMA controller 622, a blood pressure calculator 624, a display interface 626. The SMA controller 622 controls the SMA wires 608a-608e to activate (e.g., deform) the SMA wires 608a-608e or deactivate (e.g., release) the SMA wires. In particular, the SMA controller 622 applies an activation signal to the SMA wires 608a-608e, which may be in the form of a voltage or heat, thereby causing the SMA wires 608a-608e to deform to the constricting state. The SMA wires 608a-608e have a trained or memorized shape or position, which is the shape of the constricting state (FIG. 7B). As heat or voltage is applied the SMA wires 608a-608, the SMA wires 608a-608e transition to the trained shape. In some examples, once the SMA wires 608a-608e reach the trained shape, applying more voltage or heat does not further change the shape.

Once activated to the constricting state (e.g., FIG. 7b), the SMA controller 622 reduces the voltage or heat applied to the SMA wires 608a-608e, which enables the SMA wires 608a-608e to expand back to the non-constricting state (e.g., 7C) and reduce pressure on the limb of the user. While the SMA wires 608a-608e transition back to the non-constricting state, the microphone 612 detects the sounds of the blood flow through the artery. The blood pressure calculator 624 calculates the blood pressure value (e.g., the systolic and diastolic pressures) based on the corresponding voltage or heat applied by the SMA controller 622, which corresponds to a pressure applied to the limb, and the sounds detected by the microphone 612. In some examples, the blood pressure measurement is stored in the database 618. The display interface 626 and the transceiver 616 are substantially the same as the display interface 130 and the transceiver 116, respectively, of the example BP apparatus 100 of FIG. 1. Thus, to avoid redundancy, a description of the display interface 626 and the transceiver 616 are not provided herein. Similar to the example BP apparatus 100 of FIG. 1, the example BP apparatus 600 may be considered a wrist watch and can be worn on the wrist of the user, or, in other examples, the band 602 can be wider or smaller and be worn on another part of the body (e.g., the upper arm, the leg, etc.).

In general, SMAs can have different types of memory effects. Two common memory effects are the one-way memory effect and two-way memory effect. When a one-way memory effect SMA is bent or stretched, the SMA remains in the bent shape until activated (e.g., heated). Upon activating, the one-way SMA changes back to its trained or memorized shape. When the one-way memory effect SMA is deactivated (e.g., cooled), the SMA remains in the memorized shape. A two-way SMA, on the other hand, remembers two different shapes: one at a relatively high temperature and one at a relatively low temperature. Therefore, when activated (e.g., heated), the two-way memory effect SMA bends or deforms from a first shape to a second shape, and when deactivated (e.g., cooled), the two-way SMA bends or deforms back to the first shape. The SMA wire of the illustrated example may be implemented as either a one-way SMA or a two-way SMA.

In some examples, when the SMA wires 608a-608e are implemented as one-way SMAs, one or more returning members are utilized to bring the SMA wires 608a-608e back to the non-constricting position. For example, the example BP apparatus 600 of FIG. 6 includes a first spring 626 and a second spring 628 coupled to the inner surface 610 of the band 102. In the illustrated example, the first spring is disposed between the first and second SMA wires 608a, 608b and the second spring 628 is disposed between the fourth and fifth SMA wires 608d, 608e. In other examples, the first and second springs 626, 628 and the SMA wires 608a-608e may be arranged differently. In the illustrated example, the first and second springs 626, 628 are implemented as steel rings. In other examples, other types of springs may be implemented. The first and second springs 626, 628 provide a return-biasing force. As the activation signal (e.g., heat) is reduced, the force of the first and second springs 626, 628 force the band 102 and, thus, the SMA wires 608a-608e radially outwards to the non-constricting state. In other examples, no springs are used. In some instances, for example, the skin elasticity on the user's limb may be sufficient to force the band 102 (and, thus, the SMA wires 608a-608e) outward to non-constricting state.

If the SMA wire is implemented as a two-way SMA, one of the memorized shapes may correspond to the shape in the non-constricting state (e.g., FIG. 7A) and the other memorized shaped may correspond to the shape in the constricting state (e.g., FIG. 7B). Therefore, when the SMA wires 608a-608e are activated, the SMA wires 608a-608e transition to the smaller constricting state, and when the SMA wires 608a-608e are deactivated (e.g., the voltage or heat is taken away), the SMA wires 608a-608e transition back to the wider non-constricting state. Depending on the amount of activation (e.g., the amount of heat), the SMA wires 608 can be deformed to any shape between the two memorized shapes.

FIG. 8 illustrates another example blood pressure (BP) apparatus 800. The example BP apparatus 800 is incorporated into an article of clothing that is worn by a user. In particular, in the illustrated example, the BP apparatus 800 is incorporated into a long-sleeved shirt 802.

Similar to the BP apparatus 100 and 600, the example BP apparatus 800 includes an active material to apply a constrictive force around a limb of a user. In the illustrated example, the active material is implemented as an EAP band 804. The EAP band 804 may be substantially the same at the EAP 108 illustrated in FIGS. 1 and 4. Similar to the EAP 108, the EAP band 804 may be formed of a monolithic EAP structure (e.g., on continuous EAP structure) or multiple EAP cells. In the illustrated example of FIG. 8, the EAP band 804 is disposed in the fabric of the shirt 802 at or near a wrist section 806 of the shirt 802. To power and control the EAP band 804, the BP apparatus 800 includes an electronics unit 808. In some examples, the electronics unit 808 is disposed in the fabric of the shirt 802 adjacent the EAP band 804 and connected to the EAP band 804 via a wire. In other examples, the electronics unit 808 is embedded in the EAP band 804. The electronics unit 808 includes a power source 810 (e.g., a battery), an EAP controller 812, which includes a voltage applicator 814 and a pulse detector 816, and a transceiver 818. The EAP controller 812 operates substantially the same as the EAP controller 122 of the BP apparatus 100 of FIG. 1.

The EAP controller 812 may activate the EAP band 804 based on a blood pressure request from an electronic device 820, and received by the transceiver 818. The electronic device 820 may be a smart phone, a computer, a watch, or any other electronic device capable of transmitting a signal. For example, a user may request a blood pressure measurement via the electronic device 820. The electronic device 820 transmits the request, via a transceiver 822, to the transceiver 818. The EAP controller 812 activates the EAP band 804 to constrict blood flow in the user's limb and senses pulses when the blood flow is released. The EAP information (e.g., the voltage applied to the EAP band 804, the pulse(s) detected by the pulse detector 816, etc.) is transmitted by the transceiver 818 to the electronics device 820. In the illustrated example, the electronics device 820 includes a blood pressure calculator 824 that determines the blood pressure measurement (the ratio of systolic to diastolic pressure) based on the received information. The blood pressure calculator 824 operates substantially the same as the blood pressure calculator 128 of the BP apparatus 100 of FIG. 1. The electronic device 820 also includes a display interface 826 that may cause a display of the electronic device 820 to present the measured blood pressure to the user. In other examples, the blood pressure calculator 824 may be incorporated into the electronics unit 808. The electronics unit 808 and/or the electronic device 820 may include a calibrator and/or a filter, similar to the calibrator 132 and filter 134 of FIG. 1.

Figure 9:
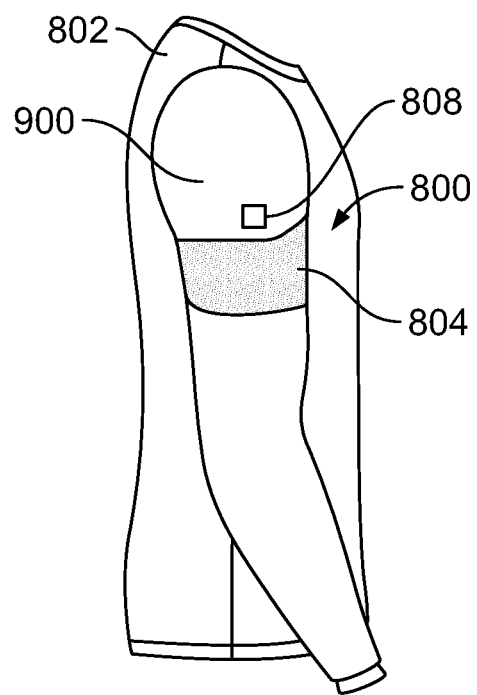
FIG. 9 shows the example blood pressure apparatus of FIG. 8 in a different location of the long-sleeve shirt.
Figure 10:
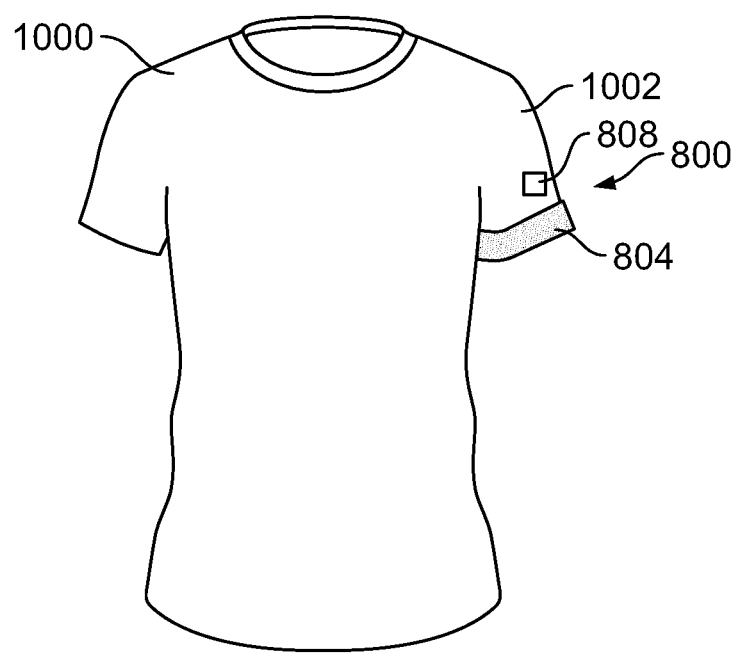
FIG. 10 shows the example blood pressure apparatus of FIG. 8 incorporated into a short-sleeve shirt.

In the illustrated example of FIG. 8, the EAP band 804 and the electronics unit 808 are disposed between the inside and outside layers of fabric of the shirt (e.g., sewn into the sleeve of the shirt). However, in other examples, the EAP band 804 and/or the electronics unit 808 may be coupled to an inside of the shirt 802, coupled to the outside of the shirt 802 or coupled to an end of the sleeve of the shirt 802. Additionally, the EAP band 804 may be disposed in other locations of the shirt 802. For example, FIG. 9 illustrates the BP apparatus 800 incorporated into an upper arm section 900 of the shirt 802, such that the EAP band 804 constricts around an upper arm of a user wearing the shirt 802. Similar to the arrangement in FIG. 8, the electronics unit 808 may be coupled to the shirt 802 adjacent the EAP band 804. Further, the BP apparatus 800 may be incorporated into other types of clothing. For example, as illustrated in FIG. 10, the BP apparatus 800 is incorporated into a short-sleeved shirt 1000. In the illustrated example of FIG. 10, the EAP band 804 is disposed at or near an end of a sleeve 1002 so that the EAP band 804 is positioned around an upper arm of a user when the shirt 1000 is worn by the user. Similar to the arrangement in FIG. 8, the electronics unit 808 may be coupled to the shirt 1000 adjacent the EAP band 804.

In the illustrated examples of FIGS. 8, 9 and 10, the active element is implemented as the EAP band 804. However, in other examples, the active element may be one or more SMA wires, similar to the SMA wires 608a-608e of the BP apparatus 600 of FIG. 6. In some such examples, one or more springs (e.g., similar to the first and second springs 626, 628) are also employed to provide a return force.

While in the illustrated examples of FIGS. 1, 6 and 8, an activation signal is applied to the active material (e.g., the EAP 108, the SMA wires 608a-608e) to morph the active from the non-constricting state (e.g., FIG. 2A) to the constricting state (e.g., FIG. 2B), in other examples, the active material may be designed to operate in reverse. For example, the active material may be designed such that applying an activation signal to the active material moves the active material outward to the non-constricting state (e.g., FIG. 2A). In such an example, an activation signal is continuously applied to the active material to hold the active material in the non-constricting state (e.g., FIG. 2A). When blood pressure is to be determined, the activation signal can be stopped, thereby enabling the active material to morph to the constricting state (e.g., FIG. 2B) to cutoff blood flow in the limb of the user. Then, to reduce pressure on the limb of the user, the activation signal can slowly be applied again, which causes the active material to morph to the non-constricting state.

While example manners of implementing the BP apparatus 100, 600 and 800 are illustrated in FIGS. 1, 6 and 8, one or more of the elements, processes and/or devices illustrated in FIGS. 1, 6 and 8 may be combined, divided, re-arranged, omitted, eliminated and/or implemented in any other way. Further, the example power source 114, the example transceiver 116, the example database 118, the example blood pressure controller 120, the example EAP controller 122, the example voltage applicator 124, the example pulse detector 126, the example blood pressure calculator 128, the example display interface 130, the example calibrator 132, the example filter 134 and/or, more generally, the example electronics unit 104 of FIG. 1; the example power source 614, the example transceiver 616, the example database 618, the example blood pressure controller 620, the example SMA controller 622, the example blood pressure calculator 624, the example display interface 626 and/or, more generally, the example electronics unit 604 of FIG. 6; and/or the example power source 810, the example EAP controller 812, the example voltage applicator 814, the example pulse detector 816, the example transceiver 818, the transceiver 822, the example blood pressure calculator 824, the example display interface 826 and/or, more generally, the example electronics unit 808 and the example electronic device 820 of FIG. 8 may be implemented by hardware, software, firmware and/or any combination of hardware, software and/or firmware. Thus, for example, any of the example power source 114, the example transceiver 116, the example database 118, the example blood pressure controller 120, the example EAP controller 122, the example voltage applicator 124, the example pulse detector 126, the example blood pressure calculator 128, the example display interface 130, the example calibrator 132, the example filter 134 and/or, more generally, the example electronics unit 104 of FIG. 1; the example power source 614, the example transceiver 616, the example database 618, the example blood pressure controller 620, the example SMA controller 622, the example blood pressure calculator 624, the example display interface 626 and/or, more generally, the example electronics unit 604 of FIG. 6; and/or the example power source 810, the example EAP controller 812, the example voltage applicator 814, the example pulse detector 816, the example transceiver 818, the transceiver 822, the example blood pressure calculator 824, the example display interface 826 and/or, more generally, the example electronics unit 808 and the example electronic device 820 of FIG. 8 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s))). When reading any of the apparatus or system claims of this patent to cover a purely software and/or firmware implementation, at least one of the example power source 114, the example transceiver 116, the example database 118, the example blood pressure controller 120, the example EAP controller 122, the example voltage applicator 124, the example pulse detector 126, the example blood pressure calculator 128, the example display interface 130, the example calibrator 132, the example filter 134, the example power source 614, the example transceiver 616, the example database 618, the example blood pressure controller 620, the example SMA controller 622, the example blood pressure calculator 624, the example display interface 626, the example power source 810, the example EAP controller 812, the example voltage applicator 814, the example pulse detector 816, the example transceiver 818, the transceiver 822, the example blood pressure calculator 824 and/or the example display interface 826 is/are hereby expressly defined to include a tangible computer readable storage device or storage disk such as a memory, a digital versatile disk (DVD), a compact disk (CD), a Blu-ray disk, etc. storing the software and/or firmware. Further still, the example BP apparatus 100, 600 and 800 of FIGS. 1, 6 and 8 may include one or more elements, processes and/or devices in addition to, or instead of, those illustrated in FIGS. 1, 6 and 8, and/or may include more than one of any or all of the illustrated elements, processes and devices.

Figure 11:
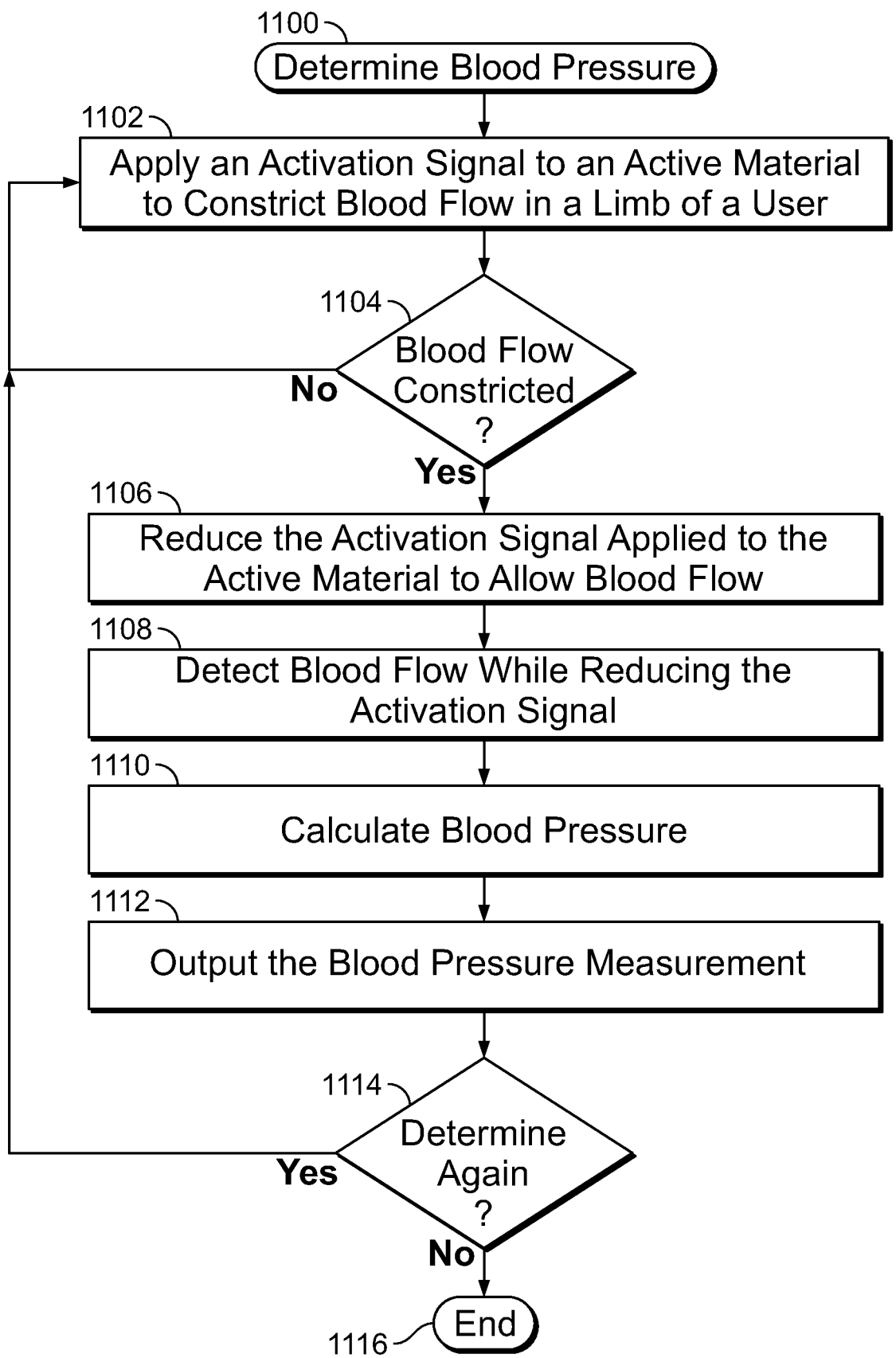
FIG. 11 is a flowchart representation of an example method to determine blood pressure as implemented by the example blood pressure apparatus of FIG. 1, 6 or 8.

A flowchart representative of example machine readable instructions for implementing the BP apparatus 100, 600 and 800 is shown in FIG. 11. In this example, the machine readable instructions comprise a program for execution by a processor such as the processor 1212 shown in the example processor platform 1200 discussed below in connection with FIG. 12. The program may be embodied in software stored on a tangible computer readable storage medium such as a CD-ROM, a floppy disk, a hard drive, a digital versatile disk (DVD), a Blu-ray disk, or a memory associated with the processor 1212, but the entire program and/or parts thereof could alternatively be executed by a device other than the processor 1212 and/or embodied in firmware or dedicated hardware. Further, although the example program is described with reference to the flowchart illustrated in FIG. 11, many other methods of implementing the example BP apparatus 100, 600 and 800 may alternatively be used. For example, the order of execution of the blocks may be changed, and/or some of the blocks described may be changed, eliminated, or combined.

As mentioned above, the example process of FIG. 11 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 11 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 11 is a flowchart representative of an example method that may be implemented by any of the BP apparatus 100, 600 or 800 to determine a blood pressure of a user. At block 1102, the example method 1100 includes applying an activation signal to an active material to constrict blood flow in a limb of a user (e.g., in an artery in the limb of the user). Applying an activation signal may include, for example, heating the active material or applying a voltage to the active material. For example, in regards to the BP apparatus 100 (FIG. 1), the voltage applicator 124 of the controller 120 applies a voltage (e.g., an activation signal) to the EAP 108, thereby causing the EAP 108 to change shape between the non-constricting state (FIG. 2A) and the constricting state (FIG. 2B) to constrict blood flow in the limb of the user. In regards to the BP apparatus 800 (FIG. 8), the voltage applicator 814 of the EAP controller 812 similarly applies a voltage to the EAP band 804. In regards to the BP apparatus 600 (FIG. 6), the SMA controller 622 of the controller 620 applies a voltage or heat (e.g., an activation signal) to the SMA wires 608a-608e to cause the SMA wires 608a-608e to change shape between the non-constricting state (FIG. 7A) and the constricting state (FIG. 7B) to constrict blood flow in the limb.

At block 1104, the example method 1100 includes determining whether blood flow is constricted (e.g., cutoff, stopped) in the limb of the user. In regards to the BP apparatus 100 (FIG. 1), for example, the pulse detector 126 may detect whether blood is flowing through the limb (e.g., based on a capacitance change in the EAP 108). In regards to the BP apparatus 800 (FIG. 8), the pulse detector 816 may similarly be used to detect whether blood is flowing through the limb. In regards to the BP apparatus 600 (FIG. 6), the microphone 612 may detect whether blood is flowing. If blood is still flowing, the example method 1100 includes continuing to apply the activation signal (block 1102) (e.g., by increasing a strength of the signal) to the active material until blood flow is constricted.

If blood flow is constricted (determined at block 1104), the example method 1100 at block 1106 includes reducing the activation signal applied to the active material to allow blood flow in the limb (e.g., in the artery). In some examples, reducing the activation signal includes reducing a strength of the activation signal (e.g., reducing a voltage or voltage amplitude, reducing heat, etc.). For example, in regards to the BP apparatus 100 (FIG. 1), the voltage applicator 124 of the controller 120 reduces the voltage or current applied to the EAP 108, which allows the EAP 108 to change shape back to the non-constricting state (FIG. 2B) and reduce the pressure applied to the limb. In regards to the BP apparatus 800 (FIG. 8), the voltage applicator 814 may similarly operate to reduce the strength of the voltage applied to the EAP band 804. In regards to the BP apparatus 600 (FIG. 6), the SMA controller 622 of the controller 620 reduces the voltage or heat applied to the SMA wires 608a-608e. If the SMA wires 608a-608e are one-way SMAs, one or more returning elements (e.g., the first and second springs 626, 628) may be implemented to force the SMA wires 608a-608e outward to relieve pressure around the limb. If the SMA wires 608a-608e are two-way SMAs, reducing the strength of the activation signal (e.g., cooling the SMA wires 608a-608e) causes the SMA wires 608a-608e to change from one shape to another shape (e.g., the non-constricting state (FIG. 7C)), thereby releasing pressure on the limb of the user.

At block 1108, the example method 1100 includes detecting blood flow in the limb while reducing the activation signal. In regards to the BP apparatus 100 (FIG. 1), the EAP 108 may be used to sense pulses generated by the blood flow (e.g., based on a capacitance change in the EAP 108). The controller 120 may detect blood flow in the limb of the user. For example, the pulse detector 126 detects a change in capacitance or voltage in the EAP 108 caused by a force from the blood flow acting on the EAP 108. Similarly, in the BP apparatus 800 (FIG. 8), the pulse detector 816 may be used to detect a change in capacitance in the EAP band 804. In regards to the BP apparatus 600 (FIG. 6), the controller 620 may detect blood flow in the arm of the user via the microphone 612, which detects the Korotkoff sounds that are indicative of blood flow phases. In other examples, other types of sensor(s) may be employed to detect blood flow in the limb of the user.

At block 1110, the example method 1100 includes calculating the blood pressure measurement of the user. In regards to the BP apparatus 100 (FIG. 1), the blood pressure calculator 128 of the controller 120 calculates the blood pressure based on the voltage applied to the EAP 108 (which is indicative of the pressure applied to the limb) and the pulses or oscillations detected by the pulse detector 126. In regards to the BP apparatus 800 (FIG. 8), the blood pressure calculator 824 similarly calculates the blood pressure measurement. In regards to the BP apparatus 600 (FIG. 6), the blood pressure calculator 624 of the controller 620 calculates the blood pressure based on the voltage or heat applied to the SMA wires 608a-608e (which is indicative of the pressure applied to the limb) and the timing of the Korotkoff sounds detected by the microphone 612.

At block 1112, the example method includes outputting the blood pressure measurement. In some examples, the blood pressure measurement (e.g., the systolic and diastolic pressures) is displayed. For example, in regards to the BP apparatus 100 (FIG. 1), the display interface 130 may cause the blood pressure measurement to be presented on the display 106. In regards to the BP apparatus 800 (FIG. 8), the blood pressure measurement may similarly be displayed on a display of the electronic device 820 via the display interface 826. In regards to the BP apparatus 600 (FIG. 6), the display interface 626 may similarly cause the blood pressure measurement to be presented on the display 606. In some examples, outputting the determined blood pressure includes transmitting the blood pressure measurement to an electronic device, such as a smart phone, a computer, etc. where the blood pressure measurement may be displayed. For example, in regards to the BP apparatus 100 (FIG. 1), the transceiver 116 may transmit the blood pressure measurement and/or other measurements from the voltage applicator 124 and the pulse detector 126 to an electronic device.

At block 1114, the example method 1100 includes determining whether to measure the blood pressure again. In some instances, the blood pressure measurement may be invalid or contain error. In such an instance, the example method 1100 can performed again. For example, in regards to the BP apparatus 100 (FIG. 1), the blood pressure calculator 128 may determine whether the blood pressure value is valid. If not, the example BP apparatus 100 may again determine the blood pressure of the user. The blood pressure calculator 624 of FIG. 6 and the blood pressure calculator 824 may make a similar determination. Otherwise, if the blood pressure is not to be determined again, the example method 1100 ends at block 1116.

Figure 12:
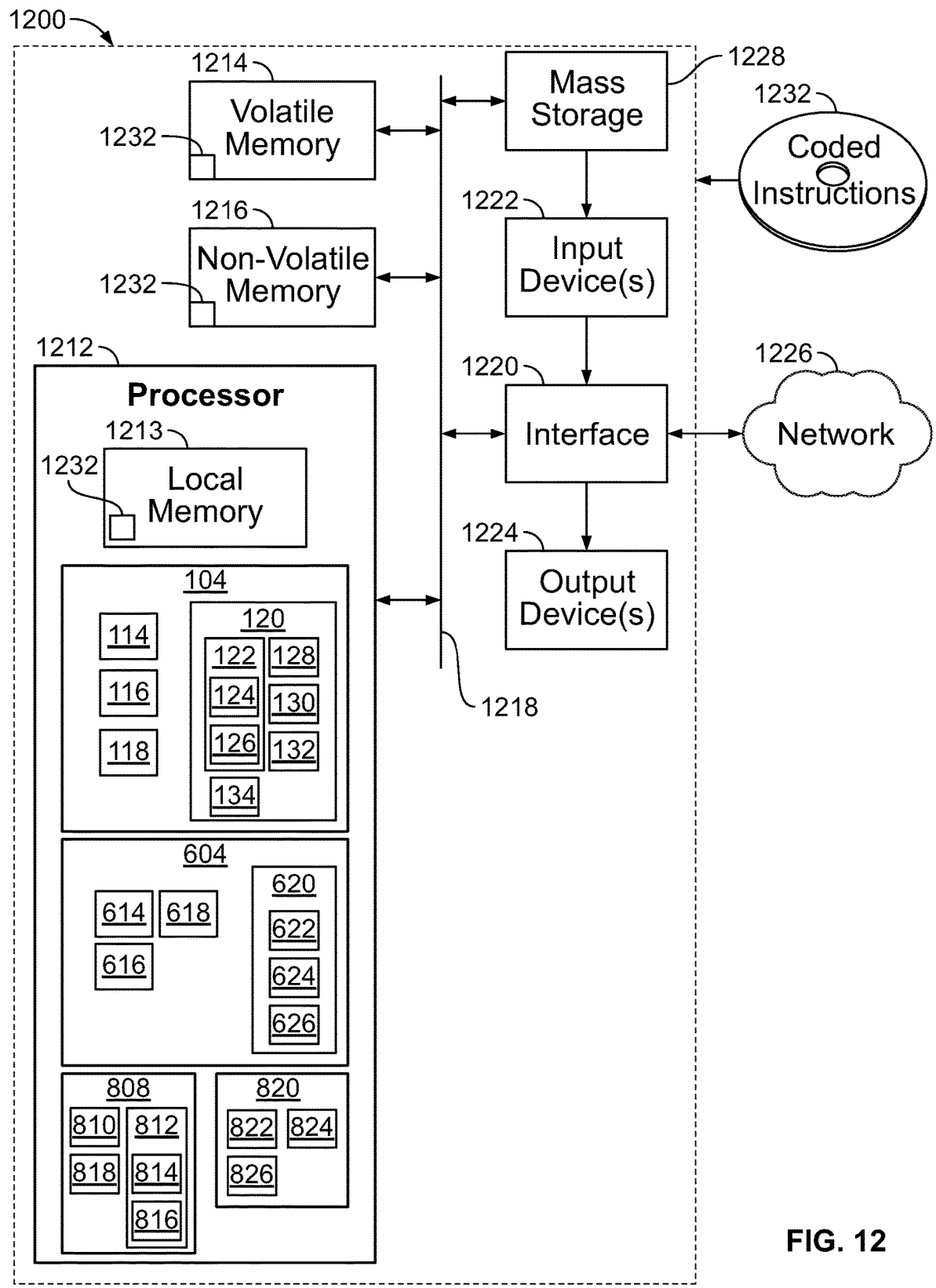
FIG. 12 is a block diagram of an example processor system structured to execute example machine readable instructions represented at least in part by FIG. 11 to implement the example blood pressure apparatus of FIGS. 1, 6 and 8.

FIG. 12 is a block diagram of an example processor platform 1200 capable of executing the instructions of FIG. 11 to implement the example BP apparatus 100, 600 and 800 of FIGS. 1, 6 and 8. The processor platform 1200 can be, for example, a server, a personal computer, a mobile device (e.g., a cell phone, a smart phone, a tablet such as an iPad™), a personal digital assistant (PDA), an Internet appliance, a DVD player, a CD player, a digital video recorder, a Blu-ray player, a gaming console, a personal video recorder, a set top box, or any other type of computing device.

The processor platform 1200 of the illustrated example includes a processor 1212. The processor 1212 of the illustrated example includes hardware that may implement one or more of the example power source 114, the example transceiver 116, the example database 118, the example blood pressure controller 120, the example EAP controller 122, the example voltage applicator 124, the example pulse detector 126, the example blood pressure calculator 128, the example display interface 130, the example calibrator 132, the example filter 134 and/or, more generally, the example electronics unit 104 of FIG. 1; the example power source 614, the example transceiver 616, the example database 618, the example blood pressure controller 620, the example SMA controller 622, the example blood pressure calculator 624, the example display interface 626 and/or, more generally, the example electronics unit 604 of FIG. 6; and/or the example power source 810, the example EAP controller 812, the example voltage applicator 814, the example pulse detector 816, the example transceiver 818, the transceiver 822, the example blood pressure calculator 824, the example display interface 826 and/or, more generally, the example electronics unit 808 and the example electronic device 820 of FIG. 8 of the BP apparatus 100, 600, 800 of FIGS. 1, 6 and 8. For example, the processor 1212 can be implemented by one or more integrated circuits, logic circuits, microprocessors or controllers from any desired family or manufacturer.

The processor 1212 of the illustrated example includes a local memory 1213 (e.g., a cache). The processor 1212 of the illustrated example is in communication with a main memory including a volatile memory 1214 and a non-volatile memory 1216 via a bus 1218. The volatile memory 1214 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1216 may be implemented by flash memory and/or any other desired type of memory device. Access to the main memory 1214, 1216 is controlled by a memory controller.

The processor platform 1200 of the illustrated example also includes an interface circuit 1220. The interface circuit 1220 may be implemented by any type of interface standard, such as an Ethernet interface, a universal serial bus (USB), and/or a PCI express interface.

In the illustrated example, one or more input devices 1222 are connected to the interface circuit 1220. The input device(s) 1222 permit(s) a user to enter data and commands into the processor 1212. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1224 are also connected to the interface circuit 1220 of the illustrated example. The output device(s) 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1220 of the illustrated example, thus, typically includes a graphics driver card, a graphics driver chip or a graphics driver processor.

The interface circuit 1220 of the illustrated example also includes a communication device such as a transmitter, a receiver, a transceiver, a modem and/or network interface card to facilitate exchange of data with external machines (e.g., computing devices of any kind) via a network 1226 (e.g., an Ethernet connection, a digital subscriber line (DSL), a telephone line, coaxial cable, a cellular telephone system, etc.).

The processor platform 1200 of the illustrated example also includes one or more mass storage devices 1228 for storing software and/or data. Examples of such mass storage devices 1228 include floppy disk drives, hard drive disks, compact disk drives, Blu-ray disk drives, RAID systems, and digital versatile disk (DVD) drives.

Coded instructions 1232 to implement the method of FIG. 11 may be stored in the mass storage device 1228, in the volatile memory 1214, in the non-volatile memory 1216, and/or on a removable tangible computer readable storage medium such as a CD or DVD.

From the foregoing, it will be appreciated that the above disclosed methods, apparatus/systems and articles of manufacture enable blood pressure to be taken via a relatively small, lightweight apparatus that may be worn by a user. The example apparatus disclosed herein are non-pneumatic devices that produce a relatively strong force to cutoff blood flow in an artery of a user. The example apparatus disclosed herein employ an active material to provide a constricting force. The active material can advantageously be incorporated into a wearable apparatus, such as a watch, or incorporated into an article of clothing. Thus, the example apparatus can be worn comfortably by a user for an extended period of time, unlike known blood pressure devices that are only used when taking blood pressure.

Although certain example methods, apparatus/systems and articles of manufacture have been disclosed herein, the scope of coverage of this patent is not limited thereto. On the contrary, this patent covers all methods, apparatus/systems and articles of manufacture fairly falling within the scope of the claims of this patent.

Example methods, apparatus/systems and articles of manufacture to constrict blood flow in a limb of a user and determine blood pressure of the user are disclosed herein. Further examples and combinations thereof include the following:

Example 1 is an apparatus to constrict blood flow in a limb of a user, the apparatus including a band to be worn around the limb of the user; an active material carried by the band; and a controller to: (1) apply an activation signal to the active material to constrict blood flow in the limb, and (2) reduce the activation signal to allow blood flow in the limb.

Example 2 includes the subject matter of Example 1, wherein the controller is to detect the blood flow in the limb while reducing the activation signal.

Example 3 includes the subject matter of Example 2, wherein the controller is to determine a blood pressure of the user based on the detected blood flow and a pressure applied to the limb by the active material.

Example 4 includes the subject matter of any of Examples 1-3, further including a display to display the blood pressure determined by the controller.

Example 5 includes the subject matter of any of Examples 1-4, wherein the active material forms a continuous loop around an inner surface of the band.

Example 6 includes the subject matter of any of Examples 1-5, wherein the active material is an electroactive polymer (EAP).

Example 7 includes the subject matter of Example 6, wherein the controller is to detect blood flow in the limb by measuring a change in capacitance of the EAP imparted by a pressure of the blood flow on the EAP.

Example 8 includes the subject matter of any of Examples 6 or 7, wherein the controller is to reduce the activation signal by reducing a voltage applied to the EAP.

Example 9 includes the subject matter of any of Examples 6-8, further including a shirt, the band coupled to a sleeve of the shirt.

Example 10 includes the subject matter of any of Examples 1-5, wherein the active material is a shape-memory alloy (SMA) wire.

Example 11 includes the subject matter of Example 10, wherein the controller is to reduce the activation signal by reducing heat applied to the SMA wire.

Example 12 includes the subject matter of any of Examples 10 or 11, wherein the SMA wire is a one-way SMA.

Example 13 includes the subject matter of Example 12, further including a spring carried by the band, the spring to provide a return-biasing force.

Example 14 includes the subject matter of any of Examples 10 or 11, wherein the SMA wire is a two-way SMA.

Example 15 includes the subject matter of any of Examples 1-14, further including a sensor to detect the blood flow in the limb of the user.

Example 16 includes the subject matter of Example 15, wherein the sensor includes at least one of a microphone, an infrared (IR) sensor, or an electroactive polymer (EAP).

Example 17 is a method to determine blood pressure of a user, the method including applying an activation signal to an active material carried by a band to be worn around a limb of the user to constrict blood flow in the limb; reducing the activation signal to allow blood flow in the limb; and calculating a blood pressure of the user.

Example 18 includes the subject matter of Example 17, further including detecting the blood flow in the limb of the user while reducing the activation signal.

Example 19 includes the subject matter of any of Examples 17 or 18, further including detecting the blood flow based on a change in capacitance of the active material.

Example 20 includes the subject matter of any of Examples 17 or 18, further including detecting the blood flow using a sensor carried by the band.

Example 21 includes the subject matter of any of Examples 17-20, wherein applying the activation signal includes applying a voltage or heat to the active material.

Example 22 includes the subject matter of any of Examples 17-21, wherein reducing the activation signal includes reducing a voltage or heat applied to the active material.

Example 23 includes the subject matter of any of Examples 17-22, further including displaying the blood pressure on a display carried by the band.

Example 24 is a computer readable storage medium including instructions that, when executed, cause a machine to at least apply an activation signal to an active material carried by a band to be worn around a limb of a user to constrict blood flow in the limb; reduce the activation signal to allow blood flow in the limb; and calculate a blood pressure of the user.

Example 25 includes the subject matter of Example 24, wherein the instructions, when executed, further cause the machine to detect the blood flow in the limb of the user while reducing the activation signal.

Example 26 includes the subject matter of any of Examples 24 or 25, wherein the instructions, when executed, cause the machine to detect the blood flow based on a change in capacitance of the active material.

Example 27 includes the subject matter of any of Examples 24 or 25, wherein the instructions, when executed, cause the machine to detect the blood flow using a sensor carried by the band.

Example 28 includes the subject matter of any of Examples 24-27, wherein the instructions, when executed, cause the machine apply the activation signal by applying a voltage or heat to the active material.

Example 29 includes the subject matter of any of Examples 24-28, wherein the instructions, when executed, cause the machine to reduce the activation signal by reducing a voltage or heat applied to the active material.

Example 30 includes the subject matter of any of Examples 24-29, wherein the instructions, when executed, cause the machine to display the blood pressure on a display carried by the band.

What is claimed is:

1. An article of clothing to be worn by a person, the article of clothing comprising:
    an active material to constrict from a first state in which the active material has a first circumference to a second state in which the active material has a second circumference smaller than the first circumference, the active material to at least partially surround a portion of a body part of the person when the article of clothing is worn by the person; and
    logic circuitry to:
        apply an activation signal to the active material to restrict blood flow in the portion of the body part of the person; and
        reduce the activation signal to reduce the restriction of the blood flow in the portion of the body part of the person;
    an inner layer of fabric; and
    an outer layer of fabric, wherein the active material and the logic circuitry are between the inner layer of fabric and the outer layer of fabric.

2. The article of clothing of claim 1, wherein the logic circuitry is near the active material and electrically coupled to the active material via a wire.

3. The article of clothing of claim 1, wherein the article of clothing is a shirt.

4. The article of clothing of claim 3, wherein the active material is at or near a wrist section of a sleeve of the shirt.

5. The article of clothing of claim 3, wherein the active material is disposed at an upper arm section of a sleeve of the shirt.

6. The article of clothing of claim 3, wherein the article of clothing is a short-sleeved shirt.

7. The article of clothing of claim 1, wherein the logic circuitry is to measure pulses generated by the blood flow in the body part of the person in a time period in which the activation signal is reduced.

8. The article of clothing of claim 7, wherein the logic circuitry is to transmit pulse information, representative of the pulses, to an electronic device.

9. The article of clothing of claim 8, wherein the logic circuitry it is to apply the activation signal to the active material in response to a request from the electronic device.

10. The article of clothing of claim 9, wherein the electronic device is a smart phone, a computer, or a watch.

11. The article of clothing of claim 1, further including a battery to power the logic circuitry.

12. The article of clothing of claim 1, wherein the active material is an electroactive polymer (EAP).

13. The article of clothing of claim 1, wherein the active material is a shape memory alloy (SMA) wire.

14. The article of clothing of claim 1, wherein the active material includes a first shape memory alloy wire and a second shape memory alloy wire, the first and second shape memory alloy wires being ring-shaped, the first and second shape memory allow wires spaced apart from each other.

15. A computer readable storage medium comprising instructions that, when executed, cause at least one machine to at least:
    apply, using logic circuitry, an activation signal to an active material to constrict blood flow in a body part of a person, the active material to, in response to the activation signal, constrict from a first state in which the active material has a first circumference to a second state in which the active material has a second circumference smaller than the first circumference, the active material carried by an article of clothing to be worn by the person, the active material and the logic circuitry between an inner layer of fabric and an outer layer of fabric;
    reduce, using the logic circuitry, the activation signal to allow blood flow in the body part;
    detect pulses generated by the blood flow in the body part; and
    transmit pulse information, representative of the pulses, to an electronic device.

16. The computer readable storage medium of claim 15, wherein the instructions, when executed, cause the at least one machine to apply the activation signal in response to a request from the electronic device.

17. The computer readable storage medium of claim 16, wherein the electronic device is a smart phone, a computer, or a watch.

18. The computer readable storage medium of claim 15, wherein the active material is an electroactive polymer (EAP), and the instructions, when executed, cause the at least one machine to detect the pulses by measuring a change in capacitance of the EAP.

19. The computer readable storage medium of claim 15, wherein the active material is a shape memory alloy (SMA) wire.

20. The computer readable storage medium of claim 15, wherein the active material includes a first shape memory alloy wire and a second shape memory alloy wire, the first and second shape memory alloy wires being ring-shaped, the first and second shape memory allow wires spaced apart from each other.

\* \* \* \* \*